United States Patent [19]

Kinanen et al.

[11] Patent Number: 4,757,968
[45] Date of Patent: Jul. 19, 1988

[54] APPARATUS FOR IMPLEMENTATION OF VERTICAL MOVEMENT OF A CHAIR, ESPECIALLY OF A PATIENT CHAIR

[75] Inventors: Ilmari Kinanen, Espoo; Matti Smalén, Klaukkala, both of Finland

[73] Assignee: Orion-Yhtymä Oy, Helsinki, Finland

[21] Appl. No.: 13,053

[22] Filed: Feb. 10, 1987

[30] Foreign Application Priority Data

Feb. 10, 1986 [FI] Finland ................................ 860602

[51] Int. Cl.⁴ ............................................ F16M 11/00
[52] U.S. Cl. ................................... 248/405; 248/125; 297/348
[58] Field of Search ................ 248/405, 406.1, 123.1, 248/125, 124, 669; 108/147, 144; 297/347, 348, 344, 345; 52/121; 254/7 R, 98, 103

[56] References Cited

U.S. PATENT DOCUMENTS

| | | | |
|---|---|---|---|
| 670,773 | 3/1901 | Fredericks | 297/347 X |
| 1,242,110 | 10/1917 | Koken | 248/405 |
| 2,942,700 | 6/1960 | Parmenter | 52/121 |
| 3,494,593 | 2/1970 | Blagg | 52/121 X |
| 3,587,886 | 6/1971 | Gano | 52/121 X |
| 3,863,406 | 2/1975 | Quick | 52/121 X |
| 4,183,689 | 1/1980 | Wirges et al. | 108/147 X |
| 4,279,398 | 7/1981 | Pregnall | 248/405 |
| 4,506,480 | 3/1985 | Murrill | 52/121 |
| 4,635,492 | 1/1987 | Uebelhart | 248/405 X |
| 4,673,155 | 6/1987 | Binder | 108/147 X |

Primary Examiner—J. Franklin Foss
Attorney, Agent, or Firm—Birch, Stewart, Kolasch & Birch

[57] ABSTRACT

An apparatus for the implementation of a vertical movement for a chair, especially a patient chair is disclosed. This apparatus comprises a lift column (1) with an upper end suitable for mounting a chair, a tubular shell construction (2) against which the lift column (1) is telescopically supported, a threaded member (5) whose rotation enables elevation and lowering of the lift column (1), and a motor (4) for rotating the threaded member (5). In the apparatus according the lift column (1) has a polygonal cross section, and it receives for each of its sides a support incorporating a spring action and sliding bearing contact by support braces (3) mounted to the inner surface of the shell construction (2). The apparatus achieves a vibration-free lift movement.

6 Claims, 1 Drawing Sheet

APPARATUS FOR IMPLEMENTATION OF VERTICAL MOVEMENT OF A CHAIR, ESPECIALLY OF A PATIENT CHAIR

BACKGROUND OF THE INVENTION

The present invention relates to an apparatus for the implementation of a vertical movement of a chair, especially of a patient chair.

The present invention is for use in systems in which vertical movement must be obtained with precision and without vibration, such as, e.g. panoramic radiography equipment.

DESCRIPTION OF THE BACKGROUND ART

In prior art methods, the vertical movement has usually been implemented by vertical movement of the radiographic equipment in relation to the patient. Thus, the vertical adjustment is performed by vertically moving a carriage along a column.

The use of the vertically moving carriage will make the actuator system, which moves the combination of the X-ray tube and the camera, ever more complicated. Also, avoidance of play in the guides, which is required to achieve a controlled movement, is difficult.

SUMMARY OF THE INVENTION

The aim of the present invention is to overcome the drawbacks of the aforementioned prior art technology and to provide a completely novel apparatus for, e.g. implementing the vertical movement of a patient chair.

The invention is based on utilizing a lift column of polygonal cross section for the chair and on supporting the column by means of a shell construction incorporating a spring action, sliding telescopically in relation to the lift column, and driving the lift column by means of a precision controllable motor, e.g. a stepping motor.

More specifically, the apparatus in accordance with the invention is characterized by a lift column whose top can be used for mounting a patient chair, a tubular shell for telescopically supporting the lift column, a threaded member for elevating the lift column and a motor for driving the threaded member. The lift column has a polygonal (six-sided) cross section with three opposed sides being supported by braces for sliding motion and for spring action lateral support. These braces are mounted to the inner surface of the shell.

The invention offers substantial benefits.

The apparatus in accordance with the invention achieves an accurate vertical movement with a minimal sideways play thanks to the spring-action support. Thus, the vertical movement does not cause an appreciable error in the horizontal movement. The vertical movement also operates at a high precision due to the stepping motor drive of the lift column.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention will be examined in more detail by means of the exemplifying embodiments in accordance with the attached drawings which are given by way of illustration only, and thus are not limitative of the present invention, and wherein.

DETAILED DESCRIPTION OF THE PREFERRED EMBODIMENTS

Figure 1:
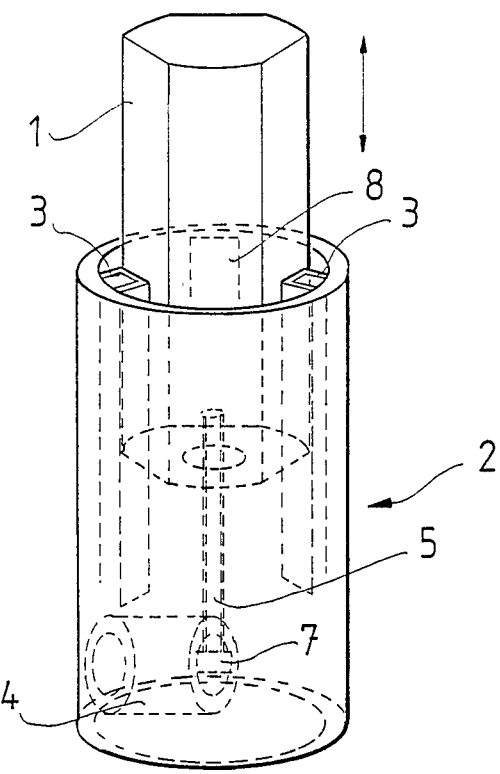
FIG. 1 shows a perspective view of a lift apparatus in accordance with the invention.
Figure 2:
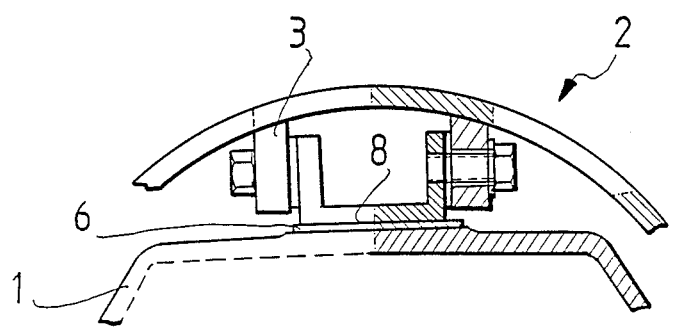
FIG. 2 shows in a partially cross-sectioned top view a support brace of the shell construction and the communication of the brace with the lift column.

FIG. 1 illustrates a construction for the implementation of an apparatus in accordance with the present invention. A tubular shell construction 2 with a round cross section has three vertical guide braces 3 attached to its inner surface and abutting a lift column 1 of polygonal cross section via slide surfaces 6. In the arrangement shown in FIG. 1, the lift column has six sides but it should readily be appreciated that a column having more than or less than six sides may be used. The slide surfaces 6 are attached to the planar sides of the lift column 1. Each support brace 3 abuts one side of the lift column 1 so that a slide area 8 between the slide surface 6 and the support brace 3 is parallel to the slide surface 6 and provides a sufficient area for achieving a desired level of durability. Mounted on its bottom, the interior of the shell construction 2 carries a motor 4, preferably a stepping motor, which is coupled via a right-angle reduction 7 to a threaded member 5, e.g. a member with a trapezoidal thread profile, which by a rotating movement inside a threaded part of the lift column 1 generates the vertical telescopic movement of the lift column 1. Furthermore, the vertical movement of the lift column 1 effects the movement of the patient chair (not shown) at the end of the lift column 1. In order to minimize play, the support braces 3 are adapted to provide a compression force between the support brace 3 and the lift column 1 which via the slide surface 6 presses the members against each other. The compression force is achieved by, for instance, adjusting the mounting position of the support braces 3. The slide surfaces 6 can be of a plastic material, preferably of polytetrafluoroethylene.

The invention is characterized by the lift column 1 being supported from three directions with a spring action by three support braces 3 providing a sliding bearing action. Consequently, the shell construction 2 need not have a round cross section but can instead be of any conceivable shape provided each support brace 3 generates a compression against the lift column 1. The slide surface 6 can also be mounted on the support brace 3.

The support braces 3 may also be an integral part to the shell construction 2, in which case the entire shell construction 2 is fabricated into a continuous profile by, e.g. extruding.

The motor 4 can also be located so that its shaft is parallel to the lift column 1, whereby the right-angle reduction 7 can be omitted.

The motor 4 can alternatively be a squirrel cage motor, in which case a feedback signal is obtained by means of, for instance, a pulse transducer mounted to the lift screw 5.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for implementation of vertical movement to an article comprising:
    a lift column upon which said article is mounted, said column having at least three sides each, comprised of a substantially flat, rectangular surface which act as slide surfaces;
    a unitary cylinder surrounding said lift column, said cylinder having at least three slide areas, each of said at least three slide areas each comprising a substantially flat, rectangular surface corresponding to one of said at least three sides such that said sides abut said slide areas, said slide areas being mounted on said cylinder such that a compression force is exerted against said at least three sides of said lift column in order to maintain said column in a vertical orientation;
    a rotatable threaded member connected to said lift column, said threaded member being rotated in order to elevate and lower said lift column, said at least three sides sliding along said corresponding at least three slide areas during elevating and lowering of said lift column; and
    a drive means for rotating said threaded member.

2. The apparatus for implementation of vertical movement as recited in claim 1 wherein said at least three sides are nonrotatable and said at least three slide areas are nonrotatable.

3. The apparatus for implementation of vertical movement as recited in claim 1 wherein each of said at least three slide areas have polytetrafluoroethylene surfaces in order to aid sliding between said at least three slide areas and said at least three sides.

4. The apparatus for implementation of vertical movement as recited in claim 1 wherein said drive means is a stepping motor.

5. The apparatus for implementation of vertical movement as recited in claim 1 wherein said at least three sides of said lift column are joined at abutting corners thereof and wherein said at least three slide areas of said cylinder contact said at least three sides on portions of said sides other than said corners.

6. The apparatus for implementation of vertical movement as recited in claim 1 wherein said article is a chair.

* * * * *